US00PP12830P2

(12) United States Plant Patent
Pannebakker

(10) Patent No.: US PP12,830 P2
(45) Date of Patent: Aug. 6, 2002

(54) *CORNUS ALBA* PLANT NAMED 'CREAM CRACKER'

(75) Inventor: John Pannebakker, Hazerswoude (NL)

(73) Assignee: Pride of Place Plants, Inc., Sidney (CA)

( * ) Notice: Subject to any disclaimer, the term of this patent is extended or adjusted under 35 U.S.C. 154(b) by 0 days.

(21) Appl. No.: 09/738,151

(22) Filed: Dec. 15, 2000

(51) Int. Cl.[7] ..... A01H 5/00
(52) U.S. Cl. ..... Plt./220
(58) Field of Search ..... Plt./220

(56) References Cited

PUBLICATIONS

UPOV–ROM GTITM Computer Database 2001/04, Feb. 6, 2001, GTI Jouve Retrieval Software, Citation for 'Cream Cracker'.*

* cited by examiner

*Primary Examiner*—Bruce R. Campell
*Assistant Examiner*—Annette H. Para
(74) *Attorney, Agent, or Firm*—Christie, Parker & Hale, LLP

(57) ABSTRACT

A *Cornus Alba* plant variety producing attractive grey green foliage with cream-colored edges.

3 Drawing Sheets

BACKGROUND OF THE INVENTION

The present invention relates to a new and distinct *Cornus Alba* plant variety which was discovered by me as a naturally occurring sport in a controlled planting of *Cornus Alba 'Gouchaulbil'*. The varietal denomination of this new variety is 'CREAM CRACKER'.

SUMMARY OF THE INVENTION

Among the novel characteristics possessed by the new variety which distinguish it from its parents and all other varieties of which I am aware are its attractive foliage.

Asexual reproduction by vegetative cuttings of the new variety as performed in Hazerswoude, The Netherlands, shows that the foregoing and other distinguishing characteristics come true to form and are established and transmitted through succeeding propagations. Other known forms of asexual reproduction may be also used.

COMPARISON WITH PARENT

The new variety produces leaves with cream colored edges whereas the parent produces leaves with golden yellow color. The inside of leaves of 'CREAM CRACKER' are grey-green in contrast to merely green color of the parent. The overall appearance of the new variety is more vivid in contrast to the duller impression given by the parent.

BRIEF DESCRIPTION OF ILLUSTRATIONS

The accompanying illustrations show typical foliage of the new variety depicted in color as nearly true as is reasonably possible to make the same in color illustrations of this character.

DESCRIPTION OF THE NEW VARIETY

The following is a detailed description of two (2) year old plants of the new variety, from specimens grown under glass in Hazerswoude, The Netherlands. The color terminology used is in accordance with The Royal Horticultural Society Colour Chart (R.H.S.C.C.), and refers to plate numbers in the aforementioned color chart. Phenotypic expression may vary depending on light, environmental and cultural conditions. It has been determined that rooting is initiated in about thirty (30) days about twenty (20° C.) degrees Celsius during the summer from layering and that a rooted cutting or liner may be produced in about twenty-five (25) days at about twenty-four (24° C.) degrees Celsius in a greenhouse.

Foliage of the new variety exhibits a creamy-yellow margin and the young growth is tinted with pink to salmon-pink color. No growth retardants have been used in the specimens described.

Plant:
- *Crop time.*—Approx. 12 months from rooted cutting to deliverable plant (30 to 40 cm).
- *Plant height.*—About 2 to 2.5 M.
- *Plant diameter or area of spread.*—About 2 M.
- *Branching habit.*—Free branching.
- *Pinching required.*—No.

Foliage:
- *Number of lateral branches.*—More than 3 per plant.
- *Lateral branch length.*—Approximately 50 cm per year.
- *Lateral branch diameter.*—Average about 6 mm.
- *Internode length.*—Average about 7 cm (2 yr. old plant).
- *Stem color.*—Near 166A later becoming more reddish (between 187A and 200C).
- *Stem pubescence.*—Very sparsely covered with short pale grey hairs.
- *Other plant/stem characteristics.*—Stems have greyish-brown lenticells that are approximately 1 mm long.

Wood:
- *New shoots.*—Near 144A.
- *Bark.*—Smooth.
- *Mature.*—Color: Near 187A. Bark: Smooth.

Leaf:
- *Leaf arrangement.*—Opposite.
- *Compound or simple.*—Simple.
- *Quantity of leaves per lateral branch.*—About 18 to 22 (average 20).
- *Edge.*—Smooth.

*Leaflet shape.*—Elliptic (sometimes slightly ovate).
*Leaflet tip.*—Apiculate.
*Leaflet base.*—Rounded (sometimes slightly attenate).
*Leaflet length.*—Between about 8 to 11 cm (average about 9.5 cm).
*Leaflet width.*—About 5 to 6 cm.
*Leaf pubescence.*—Sparsely covered with very short (less than about 0.5 mm) greyish — white hairs.
*Leaflet margin.*—Entire.
*Venation pattern.*—Pinnate, each vein is on top of leaf.
*Leaf color, young.*—Upper side: Near 138A, margins are near 1A.
*Leaf color, young.*—Underside: Near 191A.
*Leaf color, mature.*—Upper side: Between near 137C and 138A; margins near 4B.
*Leaf color, mature.*—Under side: Between near 191B margins creamy and 4C.
*Vein color.*—Upper side: Near 137C to 138A, margins are near 4B.
*Vein color.*—Underside: Near 138A margins and variegation on underside is near 4C.
*Petiole length.*—Between 1.5 and 2 cm average 1.8 cm.
*Petiole diameter.*—About 1.5 mm.
*Petiole color.*—Upper side: Near 183A.
*Petiole color.*—Underside: Near 143A.

Flower:
*Flower arrangement.*—Compound corymb.
*Flower form.*—Single.
*Flowering habit.*—Continuous from end July to mid August.
*Quantity of flowers per lateral stem.*–One compound corymb consisting of approximately 35 flowers.
*Quantity of flowers and buds per plant.*—There are about 3 lateral branches on each plant, 1 compound corymb has about 35 flowers. Each lateral branch generally consists of 1 compound corymb. Plants generally have 105 individual flowers.
*Natural flowering season.*—Summer (end July to mid August in the Netherlands).
*Rate of flower opening.*—Approximately 3 weeks.
*Fragrance.*—None.
*Flower aspect.*—Flat.
*Flower shape.*—4-parted.
*Flower diameter.*—About 5 mm.
*Flower depth (height).*—About 4 mm.
*Flower longevity on plant.*—A few days (approximately 4 to 5).
*Persistence.*—Self-cleaning.
*Peal appearance.*—Dull.
*Petal texture.*—Smooth.
*Petal arrangement.*—4-parted (cruciform).
*Petal number.*—4.
*Petals fused.*—None.
*Petal shape.*—Ovate.
*Petal margin.*—Entire.
*Petal type.*—Acute.
*Petal length.* About 2 mm.
*Petal width.*—About 1 mm.
*Petal color, when opening.*—Upper side: Near 157A.
*Petal color, fully opened.*—Underside: Near 157A.
*Petal color, when opening.*—Upper side: Near 157B.
*Petal color, fully opened.*—Underside: Near 157B.
*Petal color fading.*—Becoming slightly brownish before falling off.
*Sepal appearance.*—Campanulate base fused.
*Sepal texture.*—Smooth.
*Sepal arrangement.*—Campanulate.
*Number of sepals.*—4.
*Sepal shape.*—Fused, campanulate, with acute tips.
*Sepal margin.*—Entire.
*Sepal tip.*—Acute.
*Sepal color.*—Upper side: Green — but can't be seen from outside, and can't be measured by R.H.S. color chart.
*Sepal color.*—Underside: Near 138C.
*Calyx shape.*—Campanulate.
*Calyx length.*—About 3 mm.
*Calyx diameter.*—About 5 mm.
*Peduncle angle.*—The penduncle angle is considered 0° because it is regarded as the terminal bud which sits atop the lateral branch.
*Peduncle strength.*—Strong.
*Peduncle color.*—Between 143C and 172A.
*Flower bud length.*—About 2 mm.
*Flower bud diameter.*—About 1.5 mm.
*Flower bud shape.*—Globe-shaped to slightly ovoid.
*Time to opening.*—Approximately 1.5 weeks (10 days).
*Flower bud color.*—Between 144A and 144B; sometimes tinged pink.

Stamens, filaments and anthers:
*Stamen number.*—4, irregularly arranged around style.
*Stamen color.*—White.
*Filament color.*–White.
*Anther shape.*—Basifixed — kidney-shaped.
*Anther size.*—About 0.5 mm.
*Anther color.*—Pale brownish white too small to be measured with R.H.S. color chart.

Pollen:
*Amount of pollen.*—Few.
*Pollen color.*—Pale brown.
*Pistil number.*—1.
*Pistil length.*—About 0.75 mm.

Stigma:
*Stigma shape.*—Flattened (difficult to see).

Styles:
*Style length.*—About 0.5 mm.
*Style color.*—Whitish; too small to be measured with R.H.S. color chart.
*Ovary color.*—Greenish-white; too small to be measured with R.H.S. color chart.
*Other flower characteristics.*—Petioles are covered with very short brownish hairs — less than about 0.5 mm long.

Seeds:
*Seed development.*—Fruit set is uncommon but when it occurs, the seeds contained have a length of about 3 mm and a width of about 3 mm and are white in color.
*Hips shape.*—Globular, seeds do not protrude.
*Disease resistance and/or susceptibility.*—No susceptibility noted.

I claim:

1. A new and distinct *Cornus Alba* plant of the variety substantially as shown and described.

* * * * *

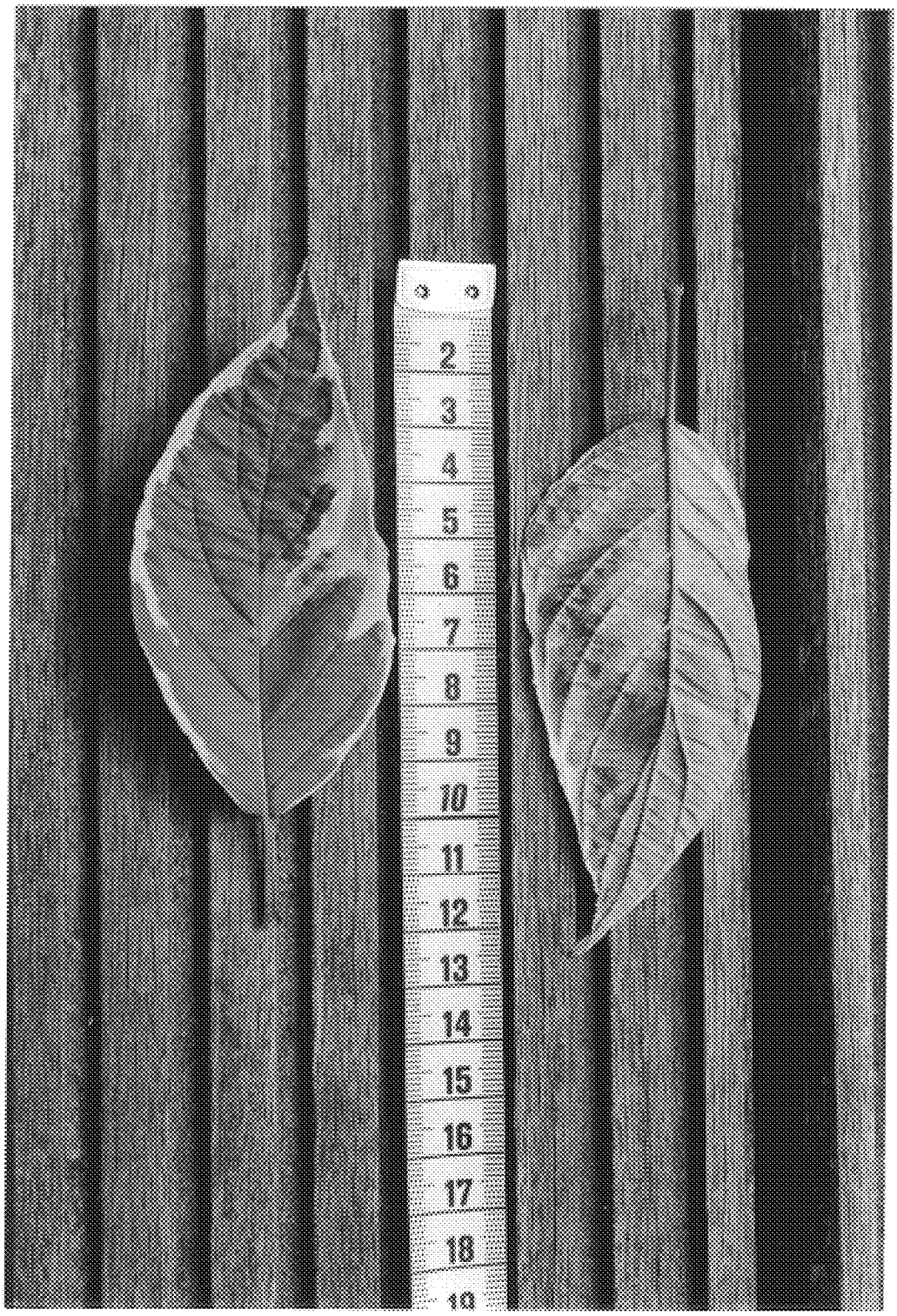
2
3
4
5
6
7
8
9
10
11
12
13
14
15
16
17
18

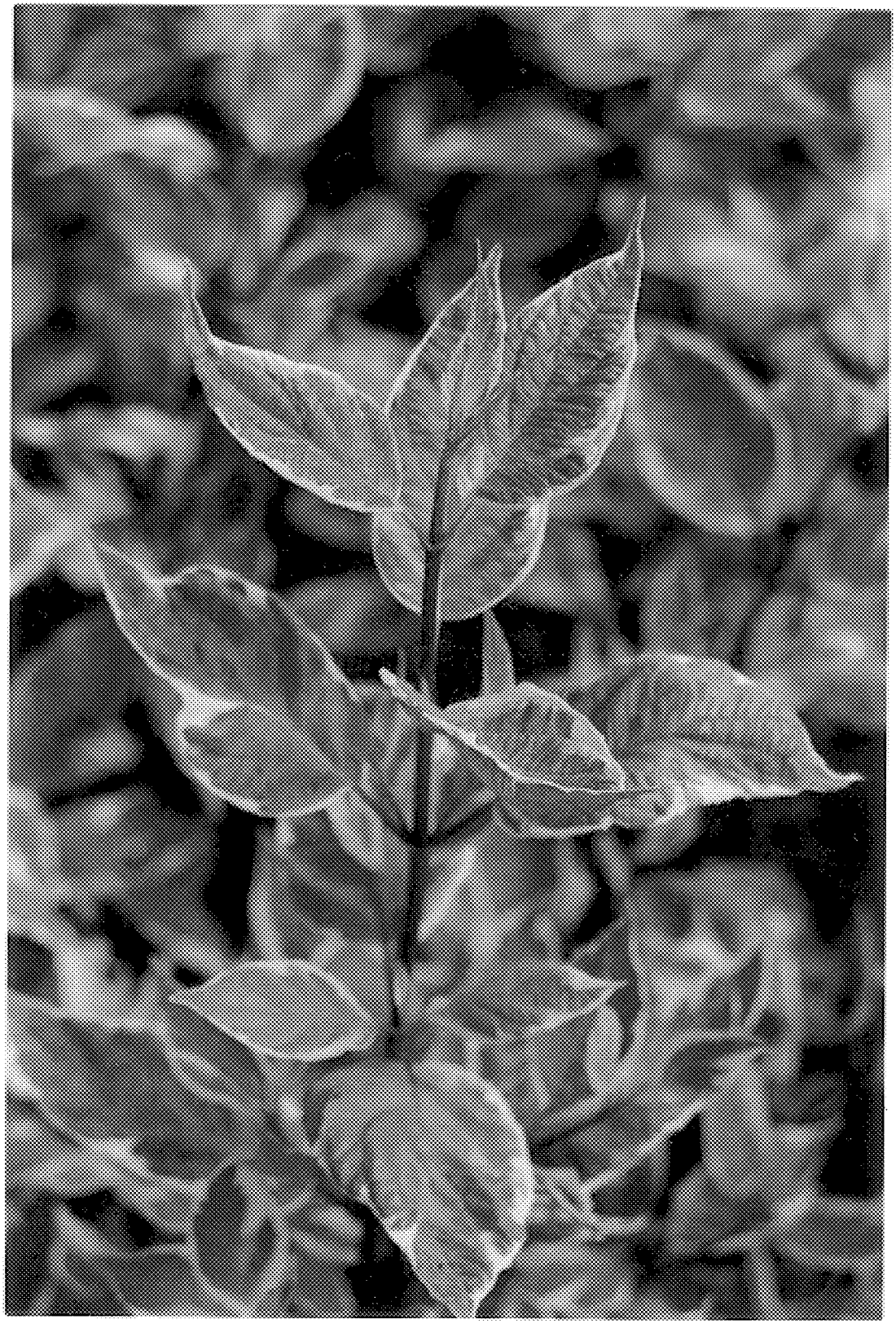

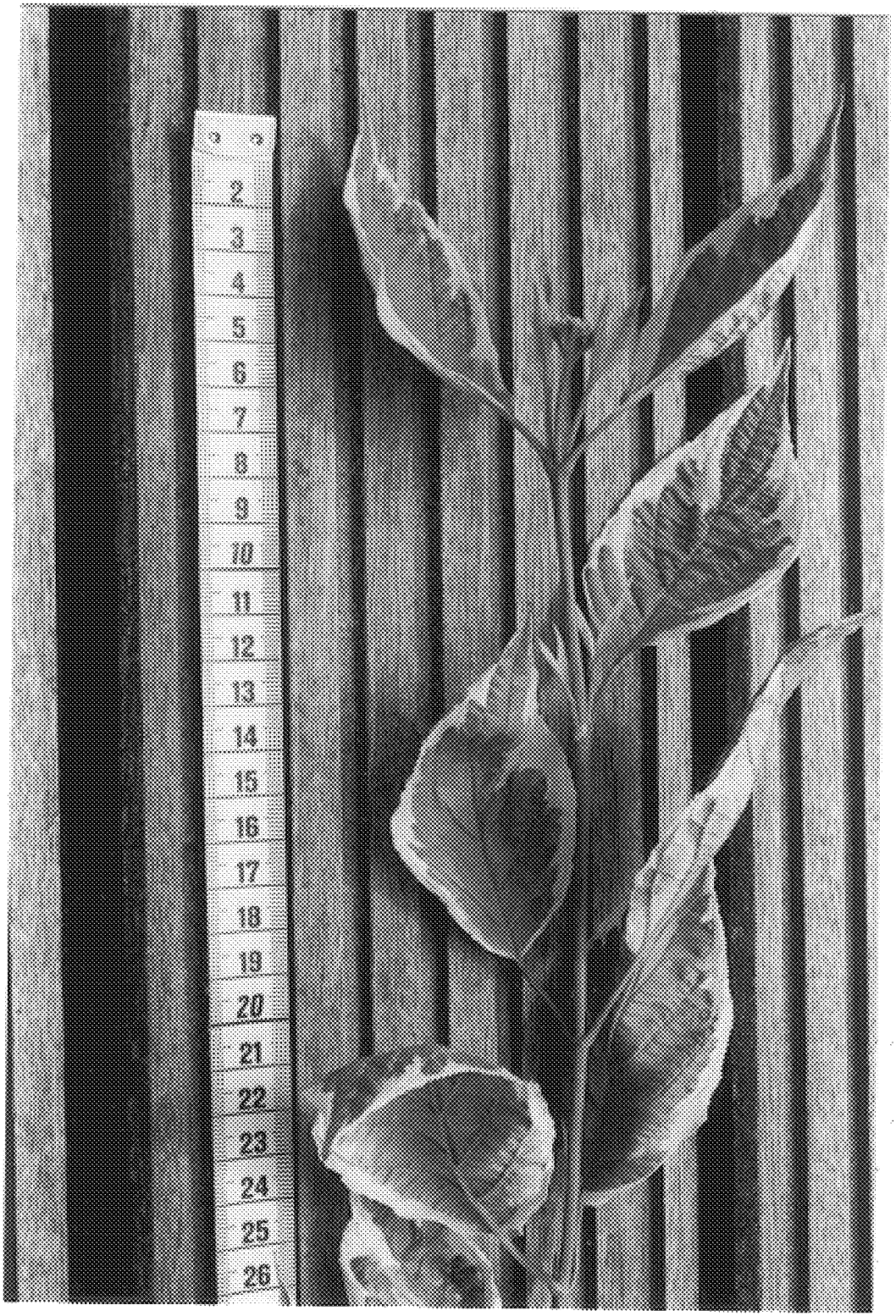
2
3
4
5
6
7
8
9
10
11
12
13
14
15
16
17
18
19
20
21
22
23
24
25
26